United States Patent [19]

Hendrix

[11] Patent Number: 4,707,454
[45] Date of Patent: Nov. 17, 1987

[54] FLUORESCENT CHLOROPHYLL LABELED ASSAY REAGENTS

[75] Inventor: John L. Hendrix, Marietta, Ga.

[73] Assignee: Bio-Diagnostics, Inc., Arlington, Tex.

[21] Appl. No.: 580,875

[22] Filed: Feb. 16, 1984

Related U.S. Application Data

[63] Continuation-in-part of Ser. No. 291,793, Aug. 10, 1981.

[51] Int. Cl.$^4$ ............................................. G01N 33/533
[52] U.S. Cl. .................................. 436/546; 436/500; 436/547; 436/800
[58] Field of Search ................... 260/245.91; 436/500, 436/547, 546, 800; 540/145

[56] References Cited

U.S. PATENT DOCUMENTS 4,331,759  5/1982  Giannini et al. ......................... 435/4
4,614,723  9/1986  Schmidt et al. ...................... 540/145

FOREIGN PATENT DOCUMENTS 2063469  6/1981  United Kingdom .

Primary Examiner—Christine M. Nucker
Assistant Examiner—Stephen C. Wieder
Attorney, Agent, or Firm—Jones, Askew & Lunsford

[57] ABSTRACT

A fluora immuno assay system. A fluorescent labeled assay reagent is prepared by conjugating an assay reagent with a fluorescent labeling agent. The fluorescent labeling agent is a chlorophyll or a porphyrin having a Stokes shift of not less than 150 nanometers. Apparatus for detecting the presence of the labeling agent comprising an excitation source illuminating a vessel with a photodetector directly within the illuminated area is also shown. The photodetector is insensitive to the spectrum of the excitation source.

5 Claims, 5 Drawing Figures

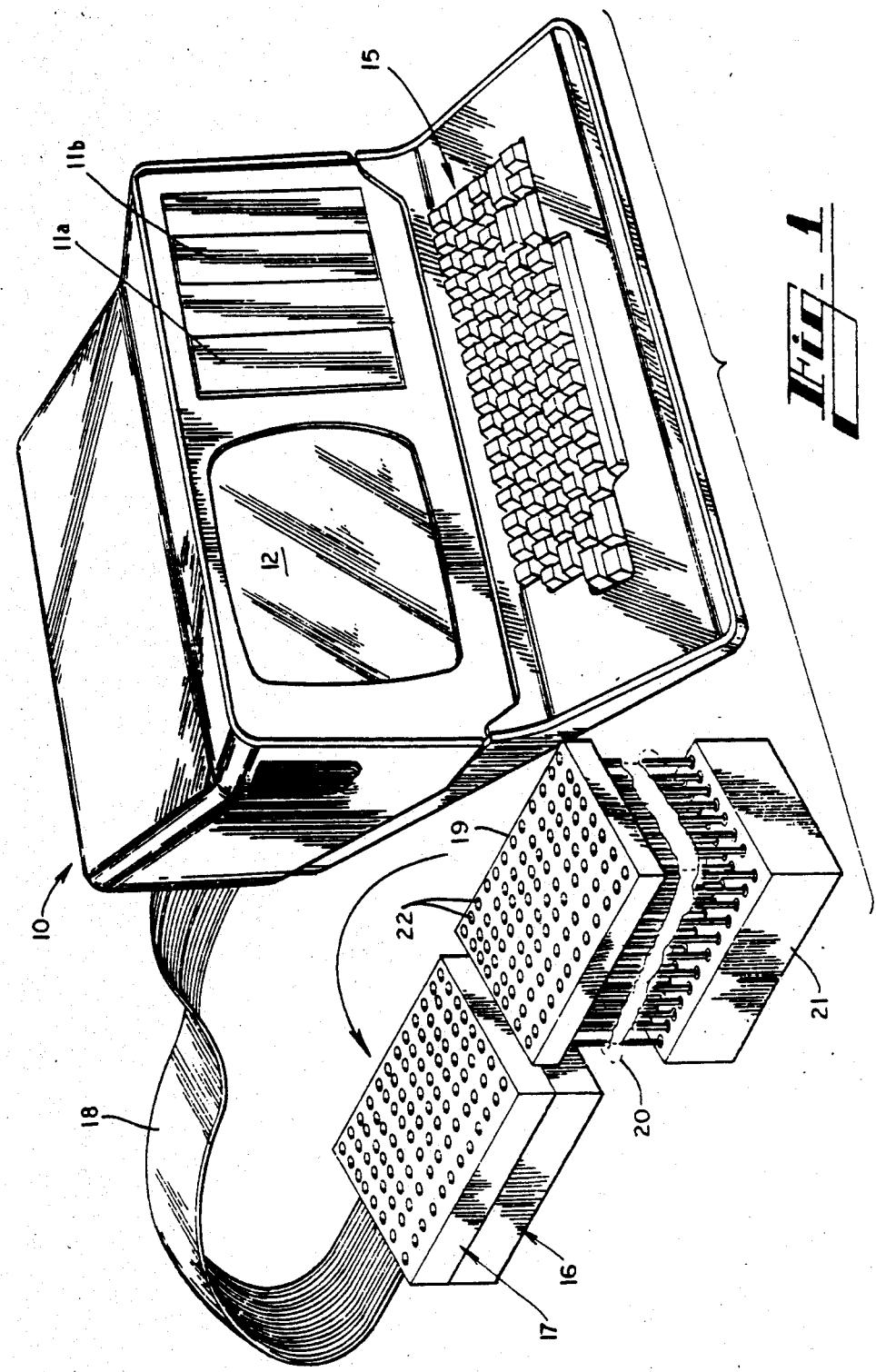

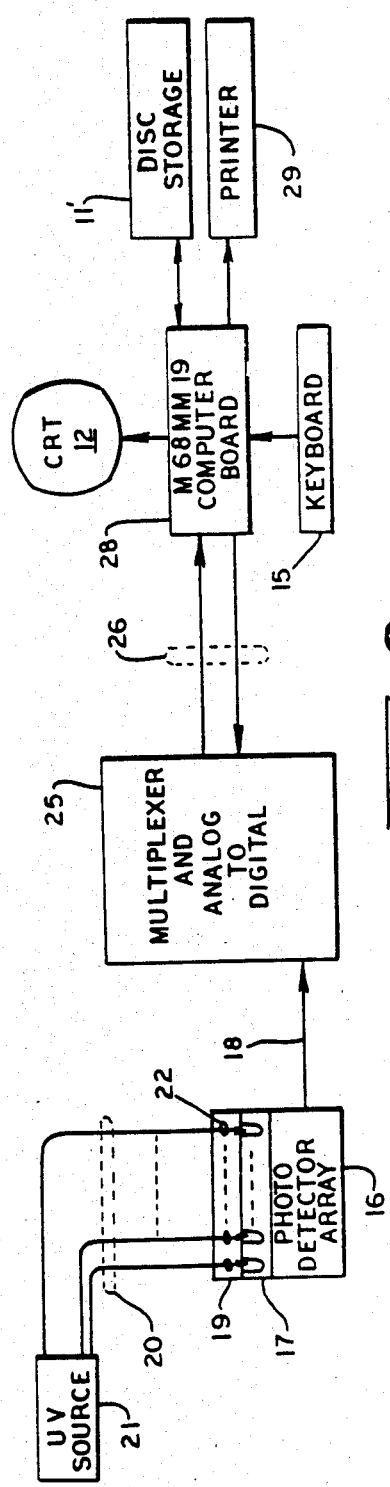
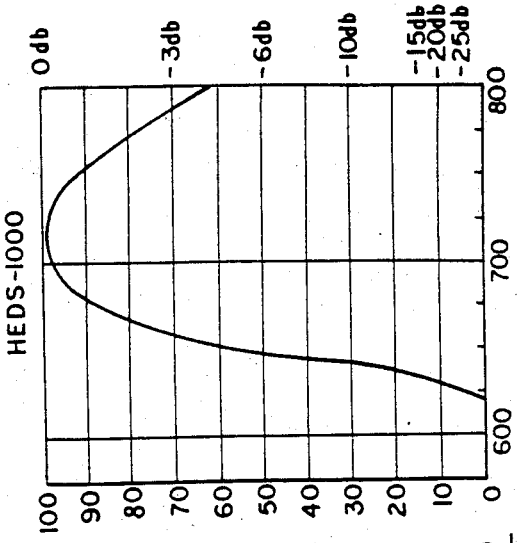
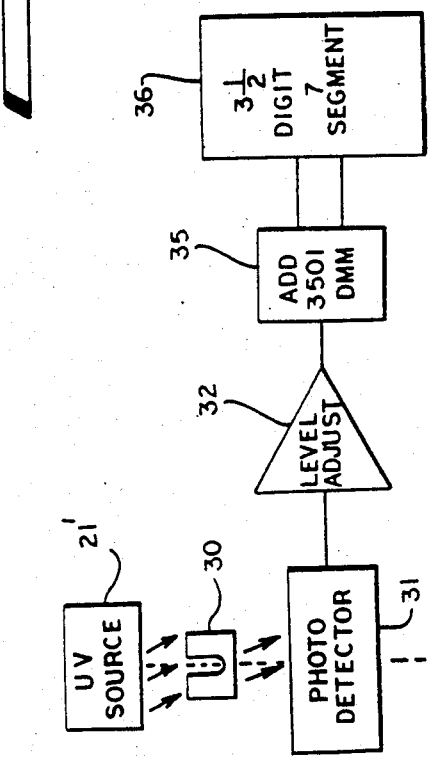

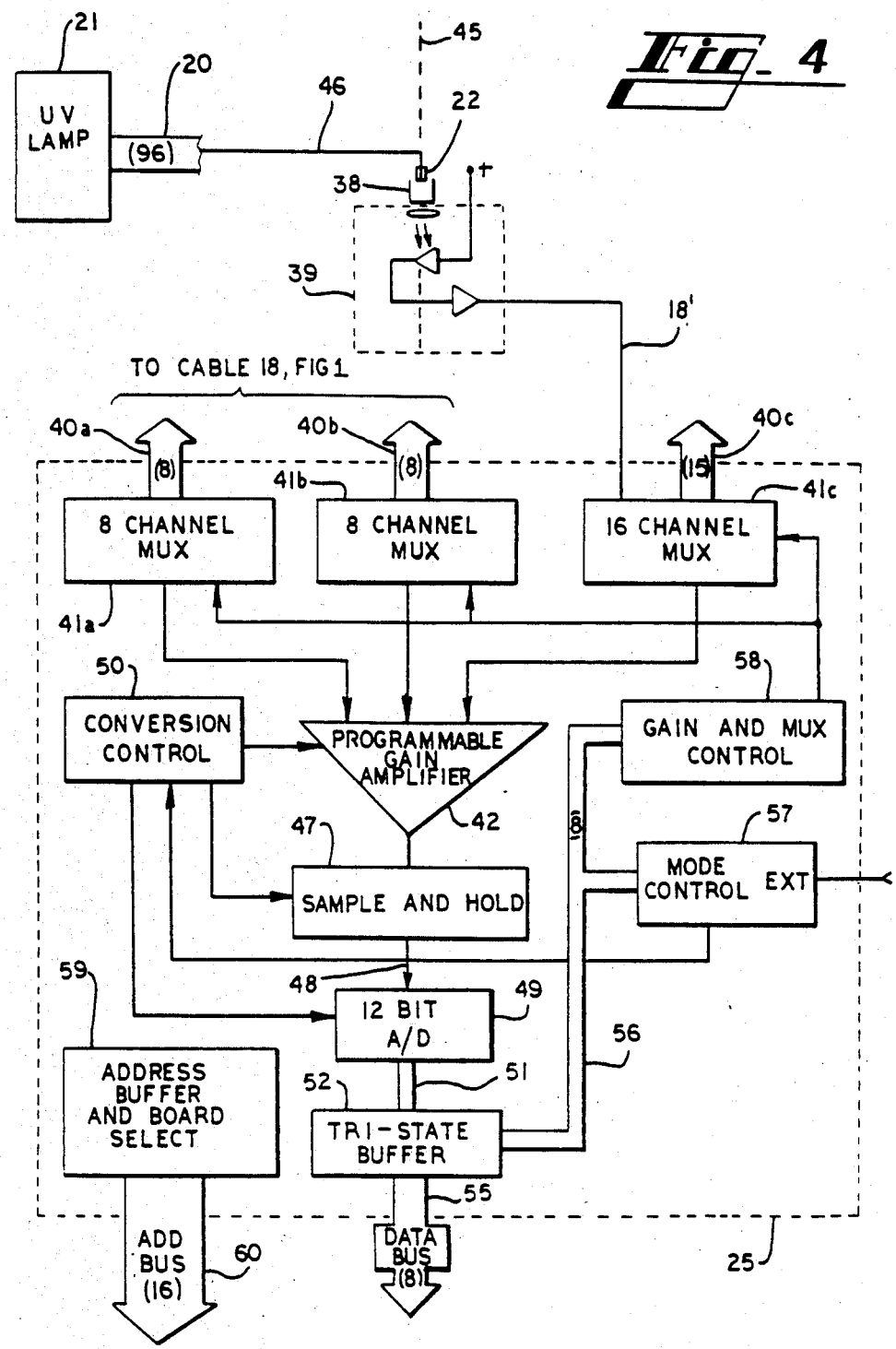
Fig_4

FLUORESCENT CHLOROPHYLL LABELED ASSAY REAGENTS

This application is a continuation-in-part of application Ser. No. 291,793, filed Aug. 10, 1981.

TECHNICAL FIELD

The present invention relates to immuno assay systems and in particular to a method of conducting fluoro immuno assays and apparatus therefor in which the fluorescent markers provide a relatively large Stokes shift from the excitation wavelength to the wavelength of fluorescent emission.

BACKGROUND OF THE INVENTION

Immuno assays are used in a wide variety of applications in the field of medicine. Such assays are tests to determine the concentrations of various substances present in blood samples taken from a patient. There are many known assays for particular substances. One of the more common classes of assays is to determine the concentration of particular hormones in a patient's blood. For example, thyroxin, also called T4, is a hormone which regulates human metabolism. It is desirable to screen all newborn babies for a shortage of T4 since such a condition can cause irreversible mental retardation if not treated. Similarly, assays for triiodothyroxine also known as T3 may be used to detect hyperthyroid conditions in patients.

Assays also exist for the presence of viruses and bacteria in a patient. Also, some modern drugs which are used to treat patients become toxic if allowed to accumulate in high concentrations in the patient's blood and, ultimately, do more harm than good. One example is the drug digoxin which is used to regulate the heart beat in cardiac patients. The problem of treatment with digoxin is that there is a wide variation from patient to patient in the amount of the drug required to produce particular concentrations in the bloodstream and excess concentrations of digoxin are toxic.

Modern immuno assay systems fall generally into three categories: (1) radio immuno assays; (2) enzyme immunoassays; and (3) fluoro immuno assays. The common feature of each is the use of marked or labeled standard solutions. A typical immuno assay scheme involves the preparation of an antibody specific to the substance (antigen) for which the test is to be conducted. Samples of the antigen are prepared by the tester which have the marker in question attached to each molecule. In the case of radio immuno assays (RIA) the labeling agent is a radioactive substance. In the case of fluoro immuno assays (FIA), the labeling agent is a material having known fluorescent qualities. Because Enzyme immunoassays are measured spectrophotometrically, they are not as sensitive as radioimmunoassays or flouro immuno assays.

The next step is to provide a dose response curve which is arrived at by mixing the labeled or antigen solution with differing concentrations of a standard unmarked antigen solution and allowing these various mixtures to compete for antibody sites in a container such as a microtiter well which has been coated with a specific antibody. The marked and unmarked antigens in the mixtures compete for the antibody sites and become attached to the antibody sites in proportion to the presence in their mixture.

The remainder of the mixture is removed from the well containing the antibodies by aspiration or some other method and then tested for the presence of the labeled antigens. Since the labeled solution was mixed with various known concentrations of unlabeled antigen, a dose response curve may be drawn, either by hand or with the aid of a computer, to correlate the output of the label detector to the concentration of the unlabeled antigens for the particular sample of marked antigen solution being used. Thus, the dose response curve provides a way of directly translating the amount of marked antigen attached to the antibody sites to the concentration of the unmarked antigen with which the marked solution was mixed.

When this has been accomplished, samples of the marked solution will be mixed with samples of patient's serum, and the marked antigen molecules will compete with the patient antigen molecules for the antibody sites. In the same fashion recited above, the patient antigen molecules and the labeled antigen molecules will compete for the available antibody sites and will be successful in proportion to their relative concentrations in the solution.

When the remainder of the solution is removed, the container is tested for the presence of the label. By using the dose response curve (which is for the particular marked solution being used) the amount of the labeled antigen which remains attached to the antibody sites will provide a direct indication off the dose response curve of the concentration of the particular antigen in the patient serum sample.

In the case of RIA, the most common label used is a radioactive isotope of iodine, $^{125}I$. In testing for the amount of labeled antigen attached to the antibody sites, the radioactive emissions from the samples must be counted in order to get a reading off the dose response curve indicative of the concentration of the antigen in the patient serum.

Radio immuno assays have become very popular in that they provide assays of very good reliability and sensitivity. The fundamental drawback of radio immuno assays is that they are quite expensive. First, the apparatus required to test for the presence of the radioactivity is complex and expensive. Secondly, the particular isotope of iodine used has a radioactive half life of sixty days. Solutions of antigens labeled with radioactive iodine must be used very shortly after preparation since their shelf life is severely limited by the rapid radioactive decay of the marker substance. It will thus be appreciated that the economics of distribution are such that only small amounts are provided to each user at any one time and must be shipped very rapidly from point of preparation to point of end use.

Also, there has been a growing reluctance on the part of many shippers, particularly airlines to transport radioactive materials.

In order to overcome these basic drawbacks of RIA techniques, fluoro immuno assays have been created. The main advantage of fluoro immuno assays over radio immuno assays is that the fluorescent compounds used as labels to be attached to antigens are very stable relative to the short radioactive half life of markers used in RIAs. Secondly, the expense of the testing apparatus for FIAs is usually less than that for RIAs and the external problems of handling radioactive materials do not arise.

The basic principle of using fluorescent labels in fluoro immuno assays is that certain materials, when illuminated by radiation in the spectrum around visible light, will emit radiation of a lower frequency (longer wavelength) in response to being so illuminated. For most fluorescent materials used in FIAs, the emitted radiation is in the spectrum of visible light, and thus detectors for detecting light may be used to ascertain the presence of the fluorescent label.

It is known that for such fluorescent materials, the frequency of the fluorescent emission is lower than the frequency of the radiation which causes the material to fluoresce. It therefore follows that the wavelength of the fluorescent emission is longer than the wavelength of the radiation illuminating the material. The difference between the wavelength of fluorescent emission and the wavelength of illumination (excitation) is referred to as the Stokes' shift. Each of the materials used as a fluorescent label has particular characteristics of required wavelength of excitation and resulting wavelength of fluorescent emission, and thus has a characteristic Stokes' shift.

There are two major drawbacks to prior art fluoro immuno assays: (1) the fluorescent marker materials used have been characterized by a relatively low Stokes' shift on the order of twenty to thirty-five nanometers; and (2) the wavelengths of fluorescent emission for the fluorescent markers are very close to the wavelengths of auto fluorescence exhibited by components which are often present in the patient's serum.

The first drawback mentioned above is one which requires very sensitive detectors and complex optical apparatus to distinguish between light having a wavelength characteristic of the fluorescent material and the light used to excite the fluorescent material. Because of the low Stokes shift, it is difficult and expensive to design light sensors which will respond to the wavelength of fluorescence and be relatively insensitive to the wavelength of the excitation light. In order to overcome this problem, many prior art fluoro immuno assay devices have used expensive defraction gratings inserted between the sample containing the fluorescent labels and the optical sensor. These are placed so that they are orthogonal to the direction of a beam of light at the excitation wavelength.

The second drawback noted above reduces the sensitivity and reliability of prior art fluoro immuno assays relative to RIAs. The presence of autofluorescing components in the serum require extra precautions and extra steps to assure that these autofluorescing substances are removed from the sample containing the antibodies before the ultimate test for presence of fluorescent material is made. This increases the complexity and expense of preparing the samples. Furthermore, it is difficult to assure removal of all of the autofluorescing substances and thus the reliability of previous fluoro immuno assays has tended to be less than that of radio immuno assays.

SUMMARY OF THE INVENTION

The present invention overcomes the drawbacks of previous fluoro immuno assays by providing fluorescent labeling material characterized by a relatively high Stokes shift. Furthermore, the assays of the present invention provide fluorescent labeling materials which fluoresce at wavelengths considerably longer than the characteristic wavelengths of most autofluorescing substances to be found in patient serum samples.

Furthermore, the present invention provides apparatus for conducting the fluoro immuno assays which is much simpler and less expensive than previous fluoro immuno assay apparatus. The present invention provides optical systems used in the signal path which are free of expensive defraction gratings and other expensive optics and for which illumination of the sensor by the excitation light source becomes irrelevant.

Thus, the present invention, by using fluorescent labeling materials characterized by both a high Stokes shift and a fluorescent wavelength far removed from the characteristic wavelengths of autofluorescing proteins, provide an FIA apparatus in which the excitation light source may be placed directly above the sample, such as a well in a microtiter plate, with the light sensors being placed directly below the well.

Since the optical transmission path of the present invention requires no defraction gratings, expensive lenses etc., the present invention also includes a simple arrangement for duplicating the optical path several times over. This provides another important aspect of the present invention, the ability to conduct large numbers of tests with a single apparatus at one time, and to automate the process of computing the dose response curve and providing quantitative results of tests on patient samples.

Accordingly, it is an object of the present invention to provide an improved fluoro immuno assay system.

It is an object of the present invention to provide an improved fluoro immuno assay apparatus with extremely simple optics.

It is a further object of the present invention to provide an automated fluoro immuno assay arrangement for which a plurality of tests may be conducted automatically, at one time, under the control of a computer.

It is a further object of the present invention to provide an automated arrangement for conducting fluoro immuno assay tests for which a plurality of samples may be tested, in sequence under the control of a computer. Furthermore, the results are multiplexed to the computer and the dose response curve, as well as the quantified results of a plurality of patient samples, are provided very rapidly.

It is a further object of the present invention to provide fluoro immuno assays for which the optical sensing signal path is characterized by at least a ten decibel drop in sensitivity from the characteristic wavelength of the label's fluorescence and the characteristic wavelength of fluorescence from common serum components.

It is a further object of the present invention to provide an automated FIA apparatus in which the outputs of a plurality of light sensors are multiplexed to an analog to digital converter with the resulting digital outputs automatically transmitted to a computer to provide quantified indications of the concentration of antigens in patient samples.

It is a further object of the present invention to provide fluorescent labeling agents useful in FIA procedures when labeling agents have relatively large Stokes and wavelengths of fluorescent emission relatively greatly removed from the wavelength of autofluorescence exhibited by protein molecules often associated with FIA procedures.

These and other objects, features and advantages of the present invention will become apparent after a review of the following detailed description of the disclosed embodiment and the appended drawings and claims.

BRIEF DESCRIPTION OF THE DRAWING

FIG. 1 is a pictorial view of a first preferred embodiment of the present invention.

FIG. 2 is a block diagram of the first preferred embodiment of the present invention.

FIG. 3 is a block diagram of a second preferred and simpler embodiment of the present invention.

FIG. 4 is a block diagram of the multiplexing arrangement of the first preferred embodiment of the present invention.

FIG. 5 is a frequency response graph of a photodetector used in constructing the preferred embodiment.

DETAILED DESCRIPTION

In carrying out the present invention, an assay reagent is labeled with a fluorescent labeling agent having a Stokes shift of not less than 150 nanometers to provide a labeled assay reagent. A labeled assay reagent is obtained by conjugating the reagent with a labeling agent. The present invention is applicable to virtually all assay reagents which are capable of conjugation with the fluorescent labeling agent of the present invention. Such assay reagents include, for example, antigens, antibodies, hormones, virus particles, haptens, bacterial components, drugs, monoclonal antibodies, anti-antibodies (also known as double antibodies or second antibodies), immuno globulins, proteins and the like. Specific assay reagents which are useful in the present invention include thyroxin, triiodothyronine, thyroid stimulating hormone, thyroxin binding globulin, thyrotropin releasing hormone, digoxin, Gentamicin, Tobramycin, Phenytoin, Theophylline, Tetracycline, Hepatitis B surface antigen, Hepatitis B core antigen, Hepatitis A antigen, Carcinoembryonic antigen, Prostatic acid phosphatase and Human chorionic gonadotropin.

The fluorescent labeling agents which are useful in the present invention include chlorophylls and porphyrins which have a Stokes shift of not less than approximately 150 nanometers.

Chlorophylls are the green pigments that are extractable by organic solvents from all autotropic and chemoautotrophic plants. Approximately ten chlorophylls have been isolated from the green parts of various plants. The most abundant green component is chlorophyll a followed by chlorophyll b, chlorophyll $c_1$, and $c_2$, chlorophyll d, protochlorophyll, bacteriochlorophylls and chlorobium chlorophylls. All of the foregoing chlorophylls have Stokes shifts greater than 150 nanometers and are useful in the present invention.

Chlorophyll a is a magnesium-complexed dihydroporphyrin with two additional hydrogen atoms at positions C-7 and C-8. Chlorophyll a is the only green pigment formed in yellow-green, blue-green and some red algae and is found in combination with small quantities of other chlorophylls in higher plants, such as Euglena, diatoms, dinoflagellates, green algae, brown algae and a few red algae. Chlorophyll a has the following structural formula:

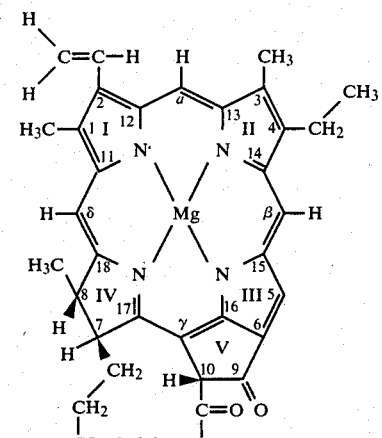

Chlorophyll a

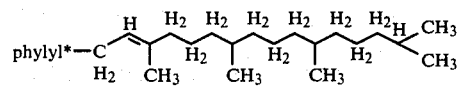

Chlorophyll b is also a dihydroporphyrin, but it differs from chlorophyll a by replacement of the methyl group at C-3 by a formyl group. Chlorophyll b occurs as the major green pigment in vascular plants, green algae and Euglena. Chlorophyll b has the following structural formula:

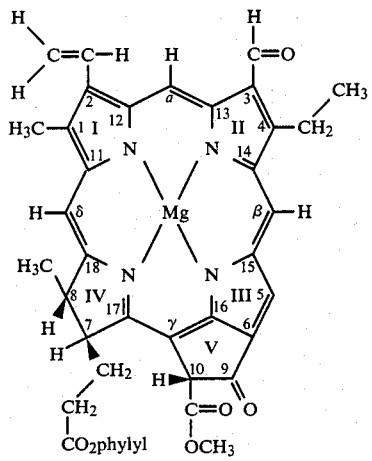

Chlorophyll b

Chlorophyll c is found in diatoms, dinoflagellates, brown algae and in certain symbiotic algae of sea anemones. Chlorophyll c occurs as a mixture of two compounds, Chlorophyll $c_1$ and $c_2$. Chlorophyll $c_1$ (Magnesium Tetradehydropheoporphyrin $a_5$ Monomethyl ester) has the following structure formula:

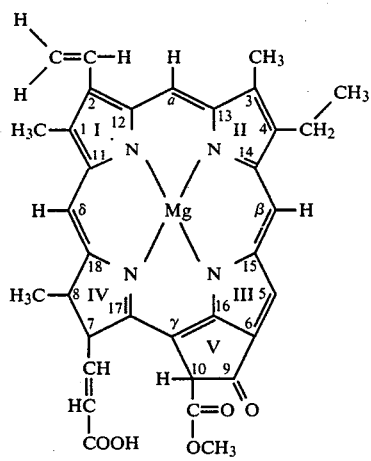

Chlorophyll c₁

Chlorophyll $c_2$ (Magnesium Hexadehydropheoporphyrin $a_5$ Monomethyl ester) has the following structural formula:

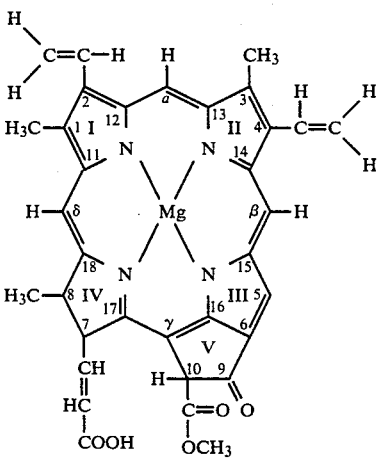

Chlorophyll c₂

Protochlorophyll may occur in either of two forms, the normal phytol ester or the free acid, protochlorophyllide. Protochlorophyll can be prepared from the oxidation of chlorophyll a with 2,3-dichloro-5,6-dicyano-1,4-benzoquinone and occurs naturally in minute quantities in yellow, etiolated seedlings grown in the dark and in the inner seed coats of cucumbers, squash and pumpkin seeds. Protochlorophyll has the following structural formula:

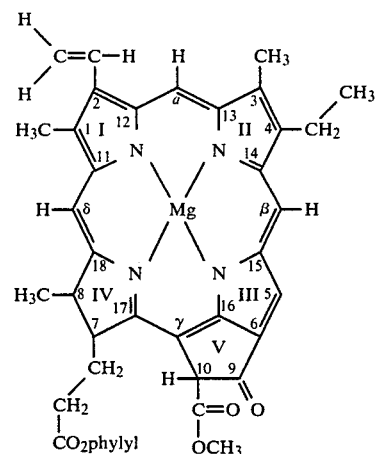

Protochlorophyll

Chlorophyll is a dihydroporphyrin (2-desvinyl-2-formyl-chlorophyll a) and occurs as the minor chlorophyll accompanying chlorophyll a in some red algae. Chlorophyll d has the following structural formula:

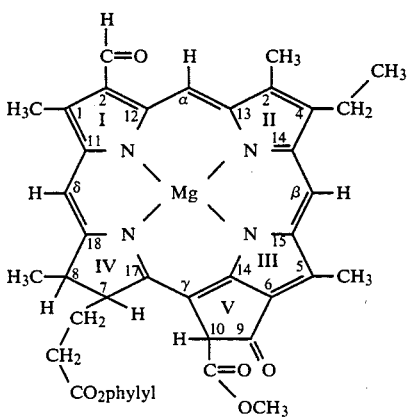

Chlorophyll d

The precise composition of chlorobium chlorophylls is unknown. Chlorobium Chlorophyll is thought to be a mixture of six different chlorophylls differing by side chain modifications. Two different chlorobium chlorophylls have been identified and are named according to the wavelength of the red absorption maxima in ether: chlorobium chlorophyll 660 and Chlorobium Chlorophyll 650. Chlorobium Chlorophylls, originally named bacterioviridin are found in the green chemoautotrophic sulfur bacteria where they are accompanied by a small amount of Bacteriochlorophyll a.

Bacteriochlorophylls are the principal chlorophylls of chemoautotropic purple sulfur bacteria (Athiorhodaceae, Thiorhodaceae and Hyphomicrobiaceae). Three chlorophyll entities are known to occur in these organisms: Bacteriochlorophyll $a_p$, Bacteriochlorophyll $a_{gg}$ and Bacteriochlorophyll b.

Bacteriochlorophyll a has the following structural formula:

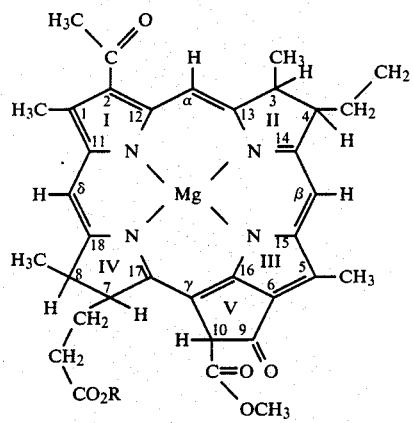

wherein R is:

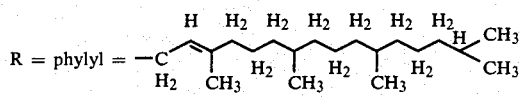

Bacteriochlorophyll $a_p$*

R = geronylgeronyl =

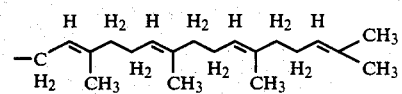

Bacteriochlorophyll $a_{gg}$*

Bacteriochorophyll $a_p$ and Bacteriochlorophyll $a_{gg}$ can be obtained from *Rhodopseudomonas palustris* (ATCC 17001) and *Rhodospirillum photometricum* (NTHC 13). Bacteriochlorophyll $a_{gg}$ is isolated as the principal green pigment from *Rhodospirillum rubrum*. Bacteriochlorophyll b is the major chorophyll found in the photosynthetic bacterium *Rhodopseudomonas viridis*.

Bacteriochlorophyll b has the following structural formula:

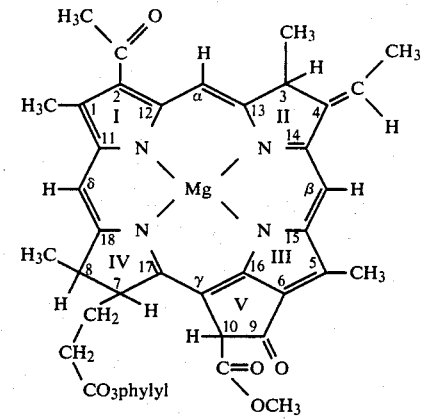

Bacteriochlorophyll b

Although all of the foregoing Chlorophylls have Stokes shifts in excess of 150 nanometers, Bacteriochlorophyll b is preferred due to its relative ease of preparation and a Stokes shift of approximately 250 nanometers. Other Chlorphylls are also useful in the present invention as long as they have Stokes shifts of not less than approximately 150 nanometers.

The absorption maxima and specific coefficients of various Chlorophylls are shown in Table 1 below:

TABLE 1

| Absorption Maxima ($\lambda_{max}$) and Specific Absorption Coefficients ($\epsilon$) of the Chlorophylls | | | | | | |
|---|---|---|---|---|---|---|
| Compound | Solvent | $\lambda_{max}$ red (nm) | $\epsilon \times 10^{-3}$ red | $\lambda_{max}$ blue (nm) | $\epsilon \times 10^{-3}$ blue | Ratio abs. blue/red | Ref. |
| Chl a | Et$_2$O | 660.5 | 96.6 | 428.5 | 125.1 | 1.30 | 114 |
| Chl a | Acetone | 663.0 | 92.6 | 430.0 | 106.0 | — | 115 |
| Chl a | Acetone (80%) | 665.0 | 90.8 | 433.0 | 101.5 | 1.21 | 116 |
| Chl a | EtOH (96%) | 665.0 | 83.4 | 432.0 | 83.2 | 1.00 | 117 |
| Chl b | Et$_2$O | 642.0 | 61.8 | 442.5 | 175.3 | 2.84 | 114 |
| Chl b | Acetone | 645.0 | 51.8 | 455.0 | 146.9 | — | 115 |
| Chl b | Acetone (80%) | 648.5 | 52.5 | 460.0 | 148.0 | 3.05 | 116 |
| Chl b | EtOH (96%) | 649.0 | 44.2 | 464.0 | 118.4 | 2.68 | 117 |
| DChl a | Et$_2$O | 659.0 | 88.6 | 428.0 | 116.1 | 1.31 | 114 |
| DChl b | Et$_2$O | 640.5 | 57.9 | 451.0 | 165.7 | 2.86 | 114 |
| Chls - | Et$_2$O | 626.5 | 29.6 | 447.3 | 262.1 | 9.10 | 4 |
| Chls c | Acetone | 628.0 | 15.8 | 442.0 | 115.9 | 7.52 | 34 |
| Chl c$_1$ | Pyridine | 639.6 | 35.0 | 461.5 | 346.0 | 9.90 | 33 |
| Chl c$_1$ | Acetone | 629.1 | 39.2 | 446.1 | 348.0 | 8.89 | 33 |
| Chl c$_2$ | Pyridine | 641.5 | 31.8 | 466.0 | 459.0 | 14.45 | 33 |
| Chl c$_2$ | Acetone | 629.6 | 37.2 | 444.6 | 321.0 | 8.62 | 33 |
| Chl d | Et$_2$O | 686.0 | 117.8 | 445.0 | 97.8 | ~0.88 | 40 |
| Protochl | Et$_2$O | 623.0 | 36.9 | 432.0 | 305.9 | 8.14 | 5 |
| Protochl | Acetone | 623.0 | 34.9 | 432.0 | 270.5 | — | 5 |
| Bchl a | Et$_2$O | 772.0 | 105.0 | 358.0 | 93.7 | 0.87 | 4 |
| Bchl a | Acetone | 775.0 | 22.1 | 358.0 | 44.2 | — | 118 |
| Bchl b | Acetone | 795.0 | — | 368.0 | — | ~0.93 | 44 |
| Chlorobium Chls 660 | Et$_2$O | 660.0 | 95.4 | 431.0 | 143.0 | ~1.58 | 4 |
| Chlorobium Cbls 650 | Et$_2$O | 650.0 | 113.5 | 425.0 | 146.0 | ~1.51 | 4 |

Alteration products or derivatives of chlorophylls are also useful in the present invention and include: chlorophyll isomers, e.g. chlorophylls a, b and d and Bacteriochlorophylls are diastereomeric at C-10; Chlorophyllides; Chlorophyllide esters; oxidized Chlorophylls, allomerized Chlorophylls, Pyrochlorophylls 9-Deoxo-9-hydroxychlorophylls; reaction with amines to provide substituted chlorin-6-amides; Chlorophyllins (saponification of chlorophylls in strongly alkaline solutions in alcohol); 2-Devinyl-2-acetylchlorophyll a.

The structures and properties of various chlorphyll a derivatives is shown in Table 2.

TABLE 2

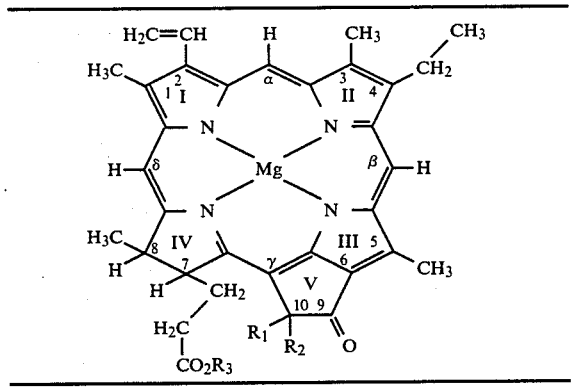

Chlorophyll α (by chromatography)
Formula: $C_{35}H_{72}O_3N_4Mg$. MW: 892.5350
Structure: $R_1 = -H$, $R_2 = -CO_2CH_3$, $R_3 = -C_{20}H_{30}$
Chlorophyll α' (by heating in pyridine)
Formula: $C_{35}H_{72}O_3N_4Mg$. MW: 892.5350
Structure: Same as Chl α with inversion around C-10
Abs. max. ether: 661.0 nm; 428.5 nm; ratio: 1.29
Chlorophyllide α (by enzymatic hydrolysis of the phytyl group)
Formula: $C_{25}H_{34}O_3N_4Mg$. MW: 614.2387
Structure: $R_1 = -H$, $R_2 = -CO_2CH_3$, $R_3 = -H$
Abs. max. ether: 660.5 nm; e, 131,000; 428 nm; e, 88,200
Methyl chlorophyllide α (by enzymatic hydrolysis in methanol)
Formula: $C_{20}H_{36}O_3N_4Mg$. MW: 628.2533
Structure: $R_1 = -H$, $R_2 = -CO_3CH_3$, $R_3 = -CH_3$
Abs. max. ether: 660.5 nm; e, 83,000; 427.5 nm; ratio: 1.30
Ethyl chlorophyllide α (by enzymatic hydrolysis in ethanol)
Formula: $C_{27}H_{38}O_3N_4Mg$. MW: 642.2690
Structure: $R_1 = -H$, $R_2 = -CO_2CH_3$, $R_3 = -CH_2CH_3$
Abs. max. ether: 660 nm; e, 89,3000; 427.5 nm; e, 119,000; ratio: 1.33
10-Hydroxychlorophyll α (by enzymatic oxidation or nonenzymatic allomerization)
Formula: $C_{35}H_{72}O_3N_4Mg$. MW: 908.5301
Structure: $R_1 = -OH$, $R_2 = -CO_2CH_3$, $R_3 = -C_{20}H_{36}$
Abs. max. ether: 660.5 nm; 428 nm; ratio: 1.29
10-Methoxychlorophyll α (by allomerization)
Formula: $C_{26}H_{74}O_3N_4Mg$. MW: 922.5457
Structure: $R_1 = -OCH_3$, $R_2 = -CO_2CH_3$, $R_3 = -C_{20}H_{36}$
Abs. max. ether: 660.5 nm; 428.5 nm
10-Methoxylactone chlorophyll α (by allomerization)
Formula: $C_{36}H_{74}O_2N_4Mg$. MW: 938.5406
Structure: $R_1 = -OCH_3$, $R_2 = -CO_2CH_3$, $R_3 = -C_{20}H_{36}$

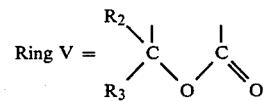

Abs. max. ether: 656 nm; 416 nm; ratio: 1.82
Pyrochlorophyll α (by prolonged heating in pyridine)
Formula: $C_{32}H_{70}O_3N_4Mg$. MW: 834.5297
Structure: $R_1 = -H$, $R_2 = -H$, $R_3 = -C_{20}H_{36}$
Abs. max. ether: 659.5 nm; e, 80,000; 429.0 nm; ratio: 1.49
Methyl pyrochlorophyllide α (by enzymatic hydrolysis and heating in pyridine)
Formula: $C_{24}H_{36}O_3N_4Mg$. MW: 570.2480
Structure: $R_1 = -H$, $R_2 = -H$, $R_3 = -CH_3$
Abs. max. ether: 659.0 nm; e, 72,000; 428.0 nm; ratio: 1.52
9-Deoxo-9-hydroxychlorophyll α (by reduction with sodium borohydride)
Formula: $C_{36}H_{74}O_3N_4Mg$. MW: 894.5506
Structure: $R_1 = -H$, $R_2 = -CO_2CH_3$, $R_3 = -C_{20}H_{36}$
—H and —OH in place of =O at C-9
Abs. max. ether: 655.0 nm; e, 53,000; 397 nm; e, 172,000; ratio: 3.25
Chlorophyll α amine products (by reaction with amines)
General Formula: $C_{35}H_{72}O_3N_4Mg$ (NR'R')
Structure: $R_1 = -H$, $R_2 = -CO_2CH_3$, $R_3 = -C_{20}H_{36}$ TABLE 2-continued

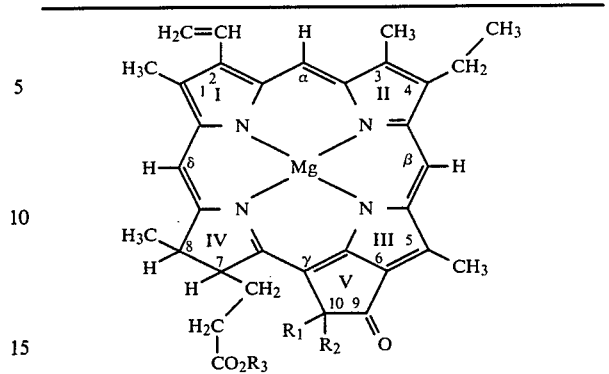

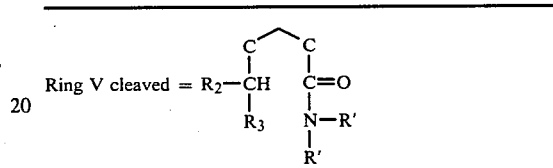

Abs. spectra of Chl α + η-propylamine, ether: 641 nm; 416 nm
2-Devinyl-2-acetylchlorophyll α (by oxidation of bacteriochorophylls)
Formula: $C_{35}H_{72}O_3N_4Mg$. MW: 908.5301
Structure: $R_1 = -H$, $R_2 = -CO_2CH_3$, $R_3 = -C_{20}H_{36}$

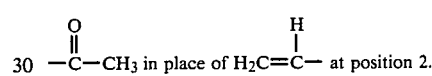

$-\overset{O}{\overset{\|}{C}}-CH_3$ in place of $H_2C=\overset{H}{\overset{|}{C}}-$ at position 2.

Abs. max. acetone: 678.5 nm; 437 nm; ratio: 2.08

The structure and properties of various magnesium-free derivatives of chlorophyll a is shown in Table 3.

TABLE 3
Structure and Properties of Magnesium-Free Chlorophyll a Derivatives

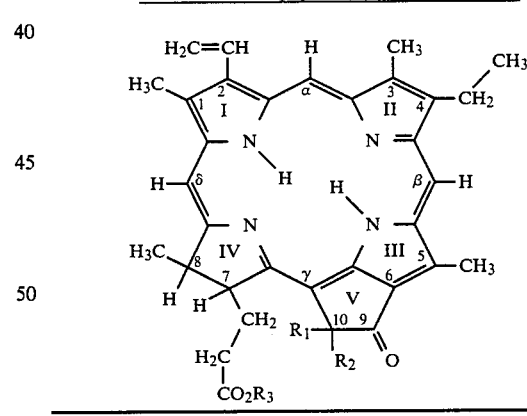

Pheophytin a (by treatment with aqueous mineral acid)
Formula: $C_{65}H_{74}O_5N_4$. MW: 870.5657
Structure: $R_1 = -H$, $R_2 = -CO_2CH_3$, $R_3 = -C_{20}H_{28}$
Abs. max. ether: 667.0 nm; e, 76,900; 409 nm; e, 156,000; ratio: 2.09
Pheophorbide a (by refluxing in acidic acetone)
Formula: $C_{25}H_{36}O_5N_4$. MW: 592.2684
Structure: $R_1 = -H$, $R_2 = -CO_2CH_3$, $R_3 = -H$
Abs. max. ether: 667.0 nm; e, 70,200; 408.5 nm; e, 141,500; ratio: 2.07
Methyl pheophorbide a (by refluxing in acidic methanol)
Formula: $C_{36}H_{28}O_5N_4$. MW: 606.2841
Structure: $R_1 = -H$, $R_2 = -CO_2CH_3$, $R_3 = -CH_3$
Abs. max. ether: 667.0 nm; e, 59,200; 408.5 nm; e, 135,000; ratio: 2.07
Pyropheophytin a (by prolong heating in pyridine and acidification)
Formula: $C_{52}H_{72}O_2N_4$. MW: 812.5603

TABLE 3-continued

Structure: $R_1 = -H$, $R_2 = -H$, $R_3 = -C_{20}H_{38}$
Abs. max. ether: 667.0 nm; e, 59,200; 408.5 nm; e, 135,000; ratio: 2.07

Methyl pyropheophorbide a (by refluxing in acidic methanol then heating in pyridine)
Formula: $C_{34}H_{36}O_2N_4$. MW: 548.2786
Structure: $R_1 = -H$, $R_2 = -H$, $R_3 = -CH_3$
Abs. max. ether: 667.0 nm; e, 52,000; 409.0 nm; ratio: 2.09

10-Hydroxypheophytin a (by allomerization and acidification)
Formula: $C_{35}H_{74}O_5N_4$. MW: 886.5606
Structure: $R_1 = -OH$, $R_2 = -CO_2CH_3$, $R_3 = -C_{26}H_{38}$

9-Deoxo-9-hydroxypheophytin a (by reduction then acidification)
Formula: $C_{55}H_{74}O_5N_4$. MW: 872.5816
Structure: $R_1 = -H$, $R_2 = -CO_2CH_3$, $R_3 = C_{20}H_{38}$
 $-H$ and $-OH$ in place of $=O$ at $C-9$
Abs. max. ether: 655 nm; e, 53,000; 397 nm; e, 172,000

Pheophytin a amine products (by acidification)
General Formula: $C_{35}H_{74}O_5N_4(NR'R'')$
Abs. spectra of pheophytin a + n-propylamine, ether: 662 nm; 441 nm Porphyrins are formally derived from porphin by substitution of some or all of the peripheral positions with various side chains. Porphin has the following structural formula:

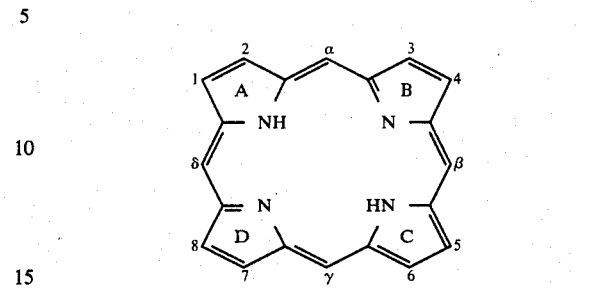

Some typical porphyrins useful in the present invention are listed in Table 4 which also gives the substituent groups and their location on the prophin structure.

TABLE 4

| Porphyrin | 1 | 2 | 3 | 4 | 5 | 6 | γ | 7 | 8 |
|---|---|---|---|---|---|---|---|---|---|
| Etioporphyrin-I | Me | Et | Me | Et | Me | Et | H | Me | Et |
| Octaethylporphyrin | Et | Et | Et | Et | Et | Et | H | Et | Et |
| Deuteroporphyrin-IX | Me | H | Me | H | Me | $P^H$ | H | $P^H$ | Me |
| Mesoporphyrin-IX | Me | Et | Me | Et | Me | $P^H$ | H | $P^H$ | Me |
| Hematoporphyrin-IX | Me | OH<br>\|<br>CH.Me | Me | OH<br>\|<br>CH.Me | Me | $P^H$ | H | $P^H$ | Me |
| Protoporphyrin-IX | Me | V | Me | V | Me | $P^H$ | H | $P^H$ | Me |
| Coproporphyrin-I | Me | $P^H$ | Me | $P^H$ | Me | $P^H$ | H | Me | $P^H$ |
| Coproporphyrin-III | Me | $P^H$ | Me | $P^H$ | Me | $P^H$ | H | $P^H$ | Me |
| Uroporphyrin-I | $A^H$ | $P^H$ | $A^H$ | $P^H$ | $A^H$ | $P^H$ | H | $A^H$ | $P^H$ |
| Uroporphyrin-III | $A^H$ | $P^H$ | $A^H$ | $P^H$ | $A^H$ | $P^H$ | H | $P^H$ | $A^H$ |
| Chlorocruoroporphyrin | Me | CHO | Me | V | Me | $P^H$ | H | $P^H$ | Me |
| Pemptoporphyrin | Me | H | Me | V | Me | $P^H$ | H | $P^H$ | Me |
| Deuteroporphyrin-IX 2,4-di-acrylic acid | Me | $Acr^H$ | Me | $Acr^H$ | Me | $P^H$ | H | $P^H$ | Me |
| 2,4-Diformyldeutero-porphyrin-IX | Me | CHO | Me | CHO | Me | $P^H$ | H | $P^H$ | Me |
| 2,4-Diacetyldeutero-porphyrin-IX | Me | Ac | Me | Ac | Me | $P^H$ | H | $P^H$ | Me |
| Deuteroporphyrin-IX 2,4-disulfonic acid | Me | $SO_3H$ | Me | $SO_3H$ | Me | $P^H$ | H | $P^H$ | Me |
| Phylloporphyrin-XV | Me | Et | Me | Et | Me | H | Me | $P^H$ | Me |
| Pyrroporphyrin-XV | Me | Et | Me | Et | Me | H | H | $P^H$ | Me |
| Rhodoporphyrin-XV | Me | Et | Me | Et | Me | $CO_2H$ | H | $P^H$ | Me |
| Phylloerythrin | Me | Et | Me | Et | Me | $CO-CH_2$ | | $P^H$ | Me |
| Desoxophylloerythrin | Me | Et | Me | Et | Me | $CH_2-CH_2$ | | $P^H$ | Me |
| Pheoporphyrin-a5 | Me | Et | Me | Et | Me | CO—CH<br>\|<br>$CO_2Me$ | | $P^H$ | Me |

Side-chain abbreviations:
Me = Methyl; Et = Ethyl; V = Vinyl; $P^H = CH_2CH_2CO_2H$;
$A^R = CH_2CO_2R$; Ac = CO.Me; $Acr^H = CH=CH.CO_2H$ Table 5 lists additional porphyrins useful in the present invention and includes the substituents thereof and spectroscopic absorption data:

TABLE 5

| Porphyrin | Substituents | | $pK_3^a$ ±0.1 unit | Band $I^b$ (nm) | $Soret^a$ (nm) |
|---|---|---|---|---|---|
| | 2 | 4 | | | |
| Meso | Et | Et | 5.8 | 620 | 399 |
| Deutero | H | H | 5.5 | 618 | 398 |
| Copro | $P^{Me}$ | $P^{Me}$ | $5.5^c$ | 620 | 399 |
| Proto | V | V | 4.8 | 630 | 408 |
| 2,4-Diacetyldeuterodioxime | C(Me)=NOH | C(Me)=NOH | 4.5 | 625 | 403 |
| 2-Formyl-4-vinyl-deuterooxime | CH=NOH | V | 4.4 | 635 | 415 |
| 2,4-Diformyldeuterodioxime | CH=NOH | CH=NOH | 4.3 | 639 | 414 |
| 4-Propionyldeutero | H | CO—Et | 4.2 | | 409 |

TABLE 5-continued

| Porphyrin | Substituents 2 | 4 | pK$_3^a$ ±0.1 unit | Band I$^b$ (nm) | Soret$^a$ (nm) |
|---|---|---|---|---|---|
| 4-Formyldeutero | H | CHO | 3.8$^c$ | 640 | 413 |
| 2-Formyl-4-vinyldeutero (chlorocruoro) | CHO | V | 3.7 | 644 | |
| 2,4-Diacetyldeutero | CO—Me | CO—Me | 3.3 | 639 | 424 |
| 2,4-Dipropionyldeutero | CO—Et | CO—Et | 3.2 | | 423 |
| 4-Nitrodeutero | H | NO$_2$ | 3.2 | | 401 |
| 2-Vinyl-4-cyanodeutero | V | CN | 3.0$^d$ | | 413 |
| 2,4-Di-methoxycarbonyl-deutero | CO$_2$Me | CO$_2$Me | 3.0$^d$ | | 423 |
| 2,4-Dibromodeutero | Br | Br | 3.0$^d$ | | |
| 2,4-Diformyldeutero | CHO | CHO | 3.0$^{c,d}$ | 651 | 436 |

$^a$Measured at 25° C. in 2.5% sodium dodecyl sulfate.
$^b$In dioxan.
$^c$By extrapolation from values at 20° C.
$^d$±0.2 units, inaccuracies introduced by ionic strength variations.

Additional prophyrins useful in the present invention include 2,4-Diacetyldeuterodioxime, 2-Formyl-4-vinyl-deuterooxime, 2,4-Diformyldeuterodioxime, 4-Propionyldeutero, 4-Formyldeutero, 2-Formyl-4-vinyl-deutero (chlorocruoro), 2,4-Diacetyldeutero, 2,4-Dipropionyldeutero, 4-Nitrodeutero, 2-Vinyl-4-cyanodeutero, 2,4-Di-methoxycarbonyl-deutero, 2,4-Dibromodeutero and 2,4-Diformyldeutero.

Alteration products, derivatives and isomers of prophyrins are also useful in the present invention and include: chlorins, phlorins, oxophlorins, corrins, corphins, corroles and etioporphyrins. Chlorins are 7,8-dihydroporphyrins. Magnesium complexes of chlorins are the chlorophylls. Chlorins have the following structural formula:

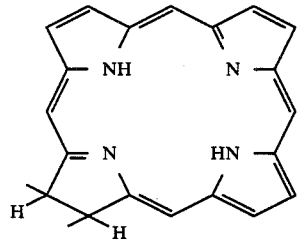

Phlorins are also dihydroporphyrins and have the following structural formula:

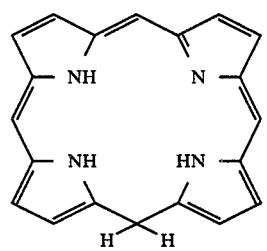

Two types of tetrahydroporphyrins are known, a- and b-tetrahydroporphyrins, and have the following structures:

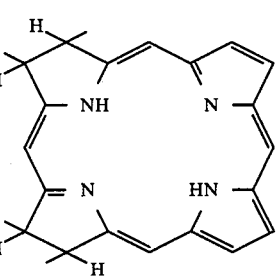
(a)

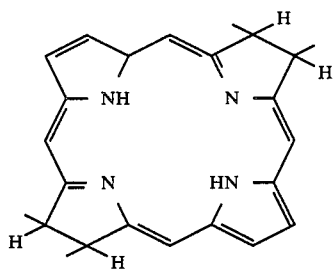
(b)

Corphins are hexahydroporphyrins and have the following structure:

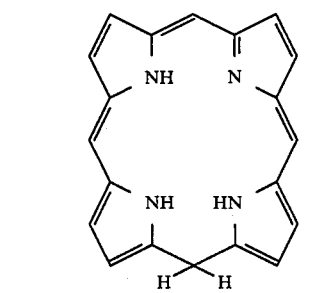

Two types of tetrahydroporphyrins are known, a- and b-tetrahydroporphyrins, and have the following structures:

(a) 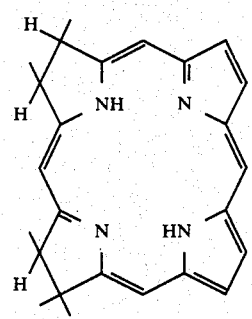

(b) 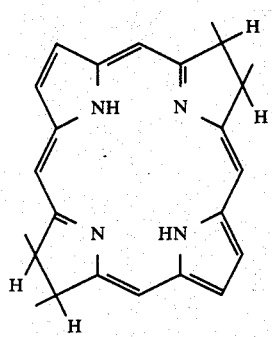

Corphins are hexahydroporphyrins and have the following structure:

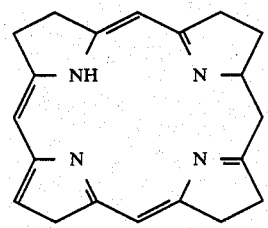

Other hexahydroporphyrins include corrins:

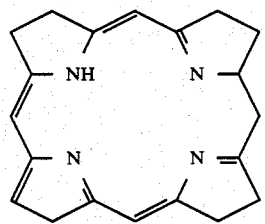

and porphyrinogens:

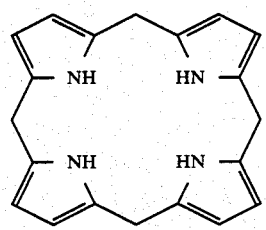

Oxophlorins are oxidized porphyrin macrocycles with oxygen functions at one to four meso-positions and have the following structures:

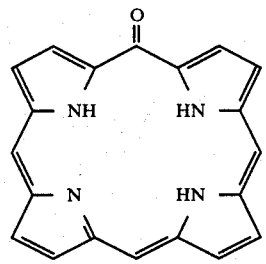

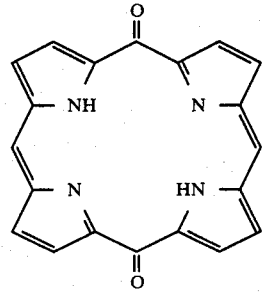

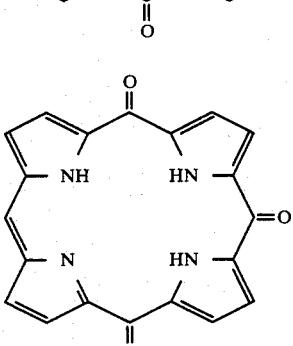

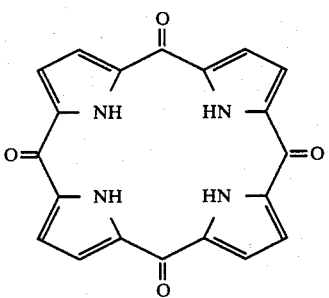

Corroles have the following structure:

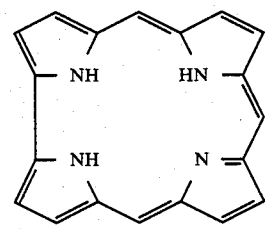

Etioporphyrins exist as four isomers and have the following structural formulas:

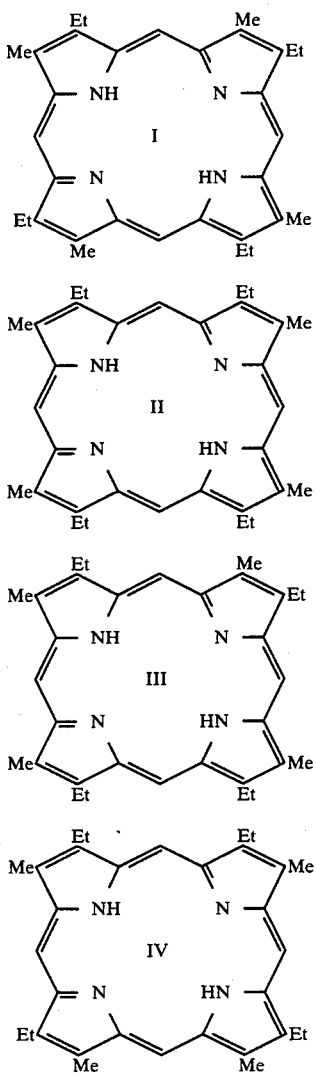

All of the foregoing porphyrins have Stokes shifts in excess of 150 nanometers and are useful in the present invention. Other porphyrins and their derivatives or alteration products are also useful in the present invention as long as they have Stokes shifts of not less than 150 nanometers.

The chlorophyll or porphyrin is chemically treated so that covalent bonding can occur with the desired hapten or antigen. A variety of immunochemicals can be used to attach the hapten or antigen ligand to a functional group on the chlorophyll or porphyrin. Activating agents that are particularly suitable for conjugation fall into two major classes (1) agents which activate carboxyl groups to form an amide bond including carbodiimides, alkyl chloroformates, and isoxazolium salts, and (2) agents which form a bond between amino groups such as diisocyanates, diimidoesters, and dihalonitrobenzenes (See Charles W. Parker, "Nature of Immunological Response and Antigen-Antibody Interaction", Chapter II in *Principles of Competitive Protein-Binding Assays*, William D. Odell and William H. Daughaday, editors, J. B. Lippincott Company, Philadelphia, 1971).

The functional group selected on the chlorophyll or porphyrin for conjugation to the ligand should be readily accessible to chemical reactivity by means of nucleophilic substitution or addition; electrophillic substitution or addition; or by forming derivatives with carbon substituents.

Cysteine and other sulfhydryl compounds have been attached to vinyl side chains on porphyrins by means of thioether linkages as noted by Sano, S. et al. (See Biochem Biophys Res Commun 15 (1964) 284-289) and Lautsch, W. et al. (See Kollid-Z. 161 (1958) 36). The carboxyl or amino groups of the cysteine can then be available for attaching the ligands.

In 1970 Warme and Hager described another method for attaching amino acids and proteins to propionic acid side chains or porphyrins. They used a sulfuric anhydride derivative as an activating intermediate and histidine and methionine as ligands to be attached to the porphyrin mesoheme (See Warme, Paul K. and Lowell P. Hager Biochemistry 9:7 (1970) 1599-1605). Other anhydride activated reactions have been previously reviewed in 1962 for organic reactions involving amide bond formation with alpha-acylamino acid mixed anhydrides (See Albertson, Noel F., "Synthesis of Peptides with Mixed Anhydrides", Chapter 4 in *Organic Reactions*, Vol. 12, Arthur C. Cope, Ed., John Wiley & Sons, New York, 1962, 157-355).

In addition, steroid compounds had been attached to peptides by means of the mixed anhydride technique (Erlanger et al., J Biol Chem 228 (1957), 713-727).

The 7-propionic acid group of chlorophylls is one of the best functional groups for attaching ligands, once the phytyl or farnesyl chains have been removed by enzymatic activity, saponification, or hydrolysis. Denniss and Sanders described a procedure in 1978 in which 3-(1-imidazolyl) prophylamine was coupled to the 7-propionic acid group of pyrochlorophyll by means of a mixed anhydride intermediate using triethylamine and ethyl chloroformate in dry tetrahydrofuran (See Denniss, Iain S. and Jeremy K. M. Sanders, Tetrahedron Letters 3 (1978), 295-298). Wright and Boxer used the 7-propionic acid group of Bacteriochlorophyllide a to form a covalent bond with apomyoglobin so as to form a synthetic subsititute for heme and determine the solution properties of the complex (See Wright, Karen A. and Steven G. Boxer, Amer Chem Soc 20:26 (1981) 7546-7556).

The following examples are illustrative of the present invention and are not intended to limit the scope of the invention. Although the examples refer to Bacteriochlorophyllide b and the 7-propionic acid group for conjugation to ligands, it is within the skill of the art to utilize other chlorophyll or porphyrin compounds and functional groups other than 7-propionic acid for attachment to ligand groups.

EXAMPLE 1

Isolation of Bacteriochlorophyll

*Rhodopseudomonas viridis*, G. Drews strain, (ATCC 19567) was obtained from the American Type Culture Collection, Rockville, Md. and inoculated into a 1.0 liter broth solution containing the following ingredients as recommended by the supplier: Na-Succinate 2.5 g, $K_2HPO_4$ 0.9 g, $KH_2]P_4$ 0.6 g, $MgSO_4.7H_2O$ 0.2 g, $(NH_4)SO_4$ 1.25 g, $CaCl_2$ 0.07 g, Ferric Citrate 0.003 g, EDTA 0.002 g, yeast extract 0.5 g, de-ionized water 1.0 liter. The pH of the solution was adjusted to 7.0. The bacteria cells were grown anaerobically at 30° C. under a tungsten lamp for five days after which time a dark green color was observed in the liquid thereby indicating prolific growth.

A modification of the procedure described in Strain, Harold H. and Walter A. Svec, "Extraction, Separation, and Isolation", Chapter 2 in *The Chlorophylls*, Vernon and Seely, editors, Academic Press, New York, 1966, 59–60, was used to extract Bacteriochlorophyll b from the bacteria cells. The cells from six liters of bacteria culture were collected by centrifugation at 1000 times gravity for 15 minutes at 2° C. and the supernatants discarded. A solution of reagent grade solvents consisting of 250 mL of methanol, 100 mL of diethyl ether, and 50 mL of petroleum ether was added to the centrifuged cells. The solvent solution turned light green indicating extraction of the pigment of the cells. The solvent solution and extracted cells were centrifuged for 15 minutes at 2° C. at 1000 times gravity and the solvent solution decanted into a 1.0 L flask. The cells were re-extracted with 100 mL of methanol and 0 mL of diethyl ether. The cell suspensions were re-centrifuged at 1000 times gravity for 15 minutes at 2° C. and the supernatants combined with the earlier extraction solution. 500 ml of de-ionized water was added to the solution. A separatory funnel was used to separate the pigments in the ether-petroleum ether solvent layer from the aqueous solution. The ether-petroleum ether solvents were then evaporated with a rotary flash evaporator. The residue was dissolved in 30 mL of dietyl ether and diluted with 150 mL of petroleum ether. The solution was transferred to a gravity chromatography column (22 mm×500 mm) containing pressed commercial powdered sugar and 3% starch to prevent caking. The column was eluted with petroleum ether and 0.5% n-propanol until a greenish zone of pigment was carried to the bottom of the column. The pigment zone was removed from the column and repacked into a fresh column of powdered sugar. Bacteriochlorophyll b was eluted with petroleum ether plus 3% ethanol. The eluant was diluted with fresh diethyl ether and washed with de-ionized water. The ether-petroleum ether layer was separated from the water and chromatographed onto a new column of powdered sugar with petroleum ether and 0.75% n-propanol as the wash liquid. The Bacteriochlorophyll b was eluted with petroleum ether and 3% ethanol. The eluant was washed with water, cooled to $-20°$ C., and crystals were collected by centrifugation. The Bacteriochlorophyll b crystals were recrystallized from 5.0 mL of chloroform by the addition of 50 mL of peteroleum ether. A yield of about 37 mg was obtained.

The abosorption spectra of the Bacteriochlorophyll b crystals were determined by following the method o Eimhjellen et al. (See Biochemical and Biophysical Res Commun 10:3 (1963) 232–236). Absorption maxima were observed at 370, 409, and 675 nanometers in acetone similar to that reported by Eimhjellen et al.

EXAMPLE 2

Removal of Phytyl Chain

The phytyl group was cleared from Bacteriochlorophyll b by means of saponification (See Oster, Gearld et al. J Am Chem Soc 86 (1964), 1309–1313). The Bacteriochlorophyll b crystals from Example 1 were dissolved in benzene and diluted 1:14 with pentane. Saponification was accomplished by adding 1.0 mL of a filtered 7% solution of KOH in methanol to 50 mL of the Bacteriochlorophyll b solution. On vigorous shaking crystals of Bacteriochlorophyllide b and other altered products precipitated out of the solution. The crystals were collected and washed with pentane and evaporated to dryness.

EXAMPLE 3

Purification and characterization of Bacteriochlorophyllide b was performed by thin layer chromatography. (See H. H. Strain and J. Sherma, J Chem Educ, 44 (1967), 235). Products from Example 2 were dissolved in acetone and applied to 20×20 cm glass thin layer chromatography plates containing silica gel 60 F-254 with a lyer thickness of 0.25 mm (EM Reagents, Gibbstown, N.J.). The plates were developed in a solvent mixture of isooctane-acetone-diethyl ether (3:1:1). After development, the plates were observed in the dark with an ultraviolet lamp and bands that fluoresced at approximately $R_f=0.3$ were scraped off the plates and extracted from the silica gel with acetone and filtered. After slow addition of de-ionized water to acetonic solution, crystals were formed. These were collected by centrifugation and dried in vacuo over calcium sulfate.

Bacteriochlorophyllide b was characterized by addition of an equal volume of 37% hydrochloric acid to a diethyl ether solution of Bacteriochlorophyllide b. This resulted in complete extraction of Bacteriochlorophyllide into the acid layer. Bacteriochlorophyll b, however, could not be extracted into the 37% HCl layer when a similar test was performed, due to the presence of the phytyl chain. (See Amer J of Botany 41 (1954) 718–722).

The Molisch phase test for determining whether the 9-keto, 10-hydrogen, and the 10-carboxymethyl groups are still intact was performed as described by A. S. Hold (See Canadian J of Biochem and Biophys 36 (1958), 439–456). A 1.0 mL solution (estimated at approximately $1\times10^{-4}M$ by using a molar extinction coefficient of $10°$ U5 as reported by trosper, et al. for Bacteriochlorophyll b (See Biochimica et Biophysica Acta 460 (1977) 318–330)) of Bacteriochlorophyllide b in diethyl ether was carefully pipetted into a test tube containing 10 microliters of a 10% methanoloic KOH solution. At the area of contact between the two solutions a yellow-brown ring appeared indicating a positive test and that the cyclopentanone ring at position V had not been oxidized, and that the 9-keto, 10-hydrogen, and 10-carboxymethyl groups had most likely not been removed.

EXAMPLE 4

Conjugation of Bacteriochlorophyllide b to Thyroxin

A solution of 10.0 mg (0.0158 mmoles) of Bacteriochlorophyllide b and 3 microliters of triethylamine in 400 microliters of N,N-dimethylformamide was cooled to $-5°$ C. in an ice/sodium chloride bath and 2.0 microliters of isobutylchloroformate was added. The solution was mixed well and left undisturbed at $-5°$ C. for 10 minutes. A solution of 12.3 mg of L-thyroxin (Sigma Chemical Company, St. Louis, Mo.) in 3.0 mL of N,N-dimethylformamide was added and the mixture heated rapidly to about 70° C., then immediately cooled. On addition of de-ionized water the product precipitated and was collected by centrifugation and filtration.

The Bacteriochlorophyllide b-thyroxin was purified as follows: The precipitated product above was dissolved in N,N-dimethylformamide and applied to 20×20 cm silica gel thin layer chromatography plates and developed as in Example 3 above. After development, the plates were observed under ultraviolet light and bands that fluoresced at approximately $R_f=0.1$ were removed and extracted from the silica gel with N,N-dimethylformamide. Upon the addition of water a precipitate was formed and collected by centrifugation and filtration.

Bacteriochlorophyllide b-thyroxin stock solution was prepared by dissolving 1.0 mg of Bacteriochlorophyllide b-thyroxin with 500 microliters of n,N-dimethylformamide and diluted to 1.0 l with a 0.05M Tris Buffered Saline (Sigma Chemical Co.) solution.

EXAMPLE 5

Thyroxine Fluoroimmunoassay

Bacteriochlorophyllide b-thyroxin assay solution was prepared by pippeting 3.58 ml aliquot of the stock solution from Example 4 into a volumetric flask and diluting to 1.0 L with Tris Buffered Saline containing 115.2 mg of 8-anilino-1-naphthalene-sulfonic acid and 87.3 mg of sodium salicylate.

To a series of rabbit anti-thyroxin serum coated tubes (Clinical Assays, Cambridge, Mass.) 10 microliters, each, of thyroxin standards containing 0,1,0,8,12, and 20 micrograms thyroxin per deciliter was pipetted in 10 microliter quantities into anti-thyroxin coated tubes. 1.0 mL of the assay solution was added to each tube. The tubes were shaken well to mix the solutions and were left undisturbed at room temperature for one hour. The solutions were then decanted, rinsed with de-ionized water, decanted again and blotted dry. 2.0 mL of N,N-dimethylformamide was pipetted into each tube to extract the Bacteriochlorophyllide b-thyroxin bound to the antithyroxin antibody sites. After one hour, the tubes were decanted into quartz curvettes and the relative fluorescence of the solutions measured. A MPF 44B Spectrofluorometer (Perkin-Elmer, Norwalk, Conn.) was used for the measurements with the xenon lamp diffraction grating excitation set at approximately 400 nanometers and fluorescence emission measured at approximately 690 nanometers. A standard curve of relative fluorescence measured for each thyroxin standard versus its concentration was constructed and concentrations for samples containing unknown quantities of thyroxin were determined by extrapolation.

EXAMPLE 5

Triiodothyronine Fluoroimmunoassay

Bacteriochlorophyllide b was prepared according to Examples 1 through 3 and then conjugated to triiodothyronine by the following method. A solution of 10.0 mg (0.0158 mmoles) of Bacteriochlorophyllide b and 3.0 microliters of triethylamine in 400 microliters of N,N-dimethylformamide was cooled to −5° C. in an ice/-sodium chloride bath and 2.0 microliters of isobutylchloroformate was added. The solution was vortexed and left undisturbed for 10 minutes. A solution of 10.3 mg of L-3,5,3'-triiodothyronine (Sigma Chemical Company) in 3.0 mL of N,N-dimethylformamide was added and the mixture heated rapidly to about 70° C., then immediately cooled. On addition of de-ionized water the product precipitated and was collected by centrifugation and filtration.

The Bacteriochlorophyllide b-triiodothyronine was purified according to Example 4.

Bacteriochlorophyllide b-triiodothyronine stock solution was prepared by solving 1 mg of Bacteriochlorophyllide b-triiodothyronine in 500 microliters of N,N-dimethylformamide and diluting to 1.0 l with 0.15M Phosphate Buffered Saline. 1.5 mL of the stock solution was diluted to 1.0 L with 0.15M Phosphate Buffered Saline to prepare the assay solution.

100 microliters of triiodothyronine standards containing, respectively, 0,0.5,1,3, and 8 ng/mL and other serum samples containing unknown concentrations of triiodothyronine were pipetted into rabbit anti-triiodothyronine serum coated tubes (Clincal Assays), in duplicate. 1.0 mL of the assay solution was added to each tube. Each tube was mixed on a vortexer and allowed to remain undisturbed for one hour in a 37° C. water bath. Each tube was then decanted and rinsed with deionized water, then decanted and blotted dry. 2.0 mL of N,N-dimethylformamide was pipetted into each tube, vortexed, and incubated one hour at room temperature. The tubes were then decanted into quartz cuvettes and the relative fluorescence measured for each sample. A standard curve was constructed and results for samples containing unknown concentration of triiodothyronine were determined by extrapolation from the standard curve.

EXAMPLE 6

Digoxin Fluoroimmunoassay

Bacteriochlorophyllide b was prepared according to Examples 1 through 3. A 10.0 mg (0.0158 mmoles) sample of Bacteriochlorophyllide b was treated with excess thionyl chloride (200 microliters) in a manner similar to that described by C. K. Chang and T. G. Traylor (see Proc Nat Acad Sci 70:9 (1973), 2647–2650) for converting the 7-propionic acid group of Pyroporphyrin XV to an acid chloride. After evacuation of the $SO_2$ and HCl, a solution of 6.2 mg of digoxigenin (Sigma Chemical Company) that was dissolved in 200 microliters of pyridine was added to the Bacteriochlorophyllide b acid chloride. The mixture was heated over steam for 10 minutes and then cooled in an ice bath. The mixture was then dilluted with 100 microliters of methanol and the solid precipitate collected by centrifugation and filtration.

Bacteriochlorophyllide b-digoxigenin was purified according to Example 4.

1.0 mg of Bacteriochlorophyllide b-digoxigenin was dissolved with 500 microliters of N,N-dimethylformamide and diluted to 1.0 L with 0.15M Phosphate Buffered Saline to make a stock solution.

250 microliters of the stock solution was then diluted to 1.0 L with 0.15M phosphate buffered saline to make the assay solution.

The Digoxin fluoroimmunoassay was performed by the following procedure. 50 microliters of digoxin standards 0,0.5,1.0,2.0, and 4.0 ng/mL, each, was pipetted, in duplicate, into rabbit anti-digoxin serum coated tubes (Clinical Assays). 50 microliter aliquots of other samples containing unknown concentrations of digoxin were pipetted, in duplicate, into additional tubes. One milliliter of the Bacteriochlorophyllide b-digoxigenin assay solution was pipetted into each tube and mixed. The tubes were incubated in a 37° C. water bath for one hour at which time they were then decanted and rinsed with de-ionized water. After blotting the tubes dry, 2.0 mL of N,N-dimethylformamide was added to each tube and incubated at room temperature for one hour. The tubes were decanted into quarz cuvettes and the relative fluorescence measured with the xenon lamp excitation wavelength set at approximately 400 nanometers and emission measured at approximately 690 nanometers. A standard curve of relative fluorescence versus concentration was constructed and the concentrations of samples containing unknown quantities of digoxin was determined by extrapolation.

The apparatus of the present invention used to perform the assays described hereinabove is shown in the drawing figures wherein like numerals reference like parts. FIG. 1 is a pictorial diagram of the first preferred embodiment of the apparatus of the present invention. The multiplexing and computing apparatus of the present invention is a conventional stand-alone microcomputer unit contained in a housing 10. A pair of minifloppy disk drives 11a and 11b are included for storage of patient records and to store other programs which the apparatus may be used to execute when not performing the functions of the present invention. The microcomputer also includes a conventional keyboard 15. The first preferred embodiment of the apparatus of the present invention using a desk top main frame including CRT display 12, disk drives 11 and keyboard 15 manufactured under the name EXORSET 30 which is currently manufactured by Motorola Semiconductor Products, Inc. of Phoenix, Ariz. The first preferred embodiment uses a Motorola-type M68MM19 one board microcomputer inserted on the main frame shown in FIG. 1. It will be appreciated by those skilled in the art that the acetonitrile, is added to the test tube to extract off the fluorescent material from the test tube wall. Each solvent solution for the standards and patient samples, which contains both marked and unmarked antigen-antibody complexes, is exposed to radiation of a wavelength sufficient to excite the fluorescent material and the emitted radiation therefrom is measured. The concentration of the tyroxine in the patient sample can then be determined.

The apparatus of the present invention used to perform the assays described hereinabove is shown in the drawing figures wherein like numerals reference like parts. FIG. 1 is a pictorial diagram of the first preferred embodiment of the apparatus of the present invention. The multiplexing and computing apparatus of the present invention is a conventional stand-alone microcomputer unit contained in a housing 10. A pair of minifloppy disk drives 11a and 11b are included for storage of patient records and to store other programs which the apparatus may be used to execute when not performing the functions of the present invention. The microcomputer also includes a conventional keyboard 15. The first preferred embodiment of the apparatus of the present invention using a desk top main frame including CRT display 12, disk drives 11 and keyboard 15 manufactured under the name EXORSET 30 which is currently manufactured by Motorola Semiconductor Products, Inc. of Phoenix, Ariz. The first preferred embodiment uses a Motorola-type M68MM19 one board microcomputer inserted on the main frame shown in FIG. 1. It will be appreciated by those skilled in the art that the M68MM19 is a one board microcomputer using an MC6809 central processing unit interfacing to a sixteen bit system address bus, an eight bit system data bus and a fifteen bit system control bus.

The one board microcomputer also includes buffered eight and four bit parallel input/output ports and a serial input/output port which may be configured for either the RS232C or RS422 standards promulgated by the Electronics Institute of America. The microcomputer further includes direct plug-in sockets for up to 16 K of read only memory.

It should be understood that the read only memory of the microcomputer used in the first preferred embodiment is programmed to calculate both dose response curves and the patient antigen levels as described herein. The calculations of these parameters are known to those skilled in the art and the routines for calculating same are not considered novel per se.

Connected to microcomputer 10 shown in FIG. 1 is an eight by twelve array 16 of photodetectors upon which is placed an eight by twelve microtitration multi well plate 17.

Each photo sensor of the array of photosensors 16 is characterized by having a frequency response within the following parameters. The photodetectors must exhibit a substantial response to light having a wavelength of 680 nanometers. Using the response 680 nanometers as a 0 dB reference, the electrical output of the photodetector must be at least 10 dB down in response to light at 560 nanometers. This requirement assumes equal luminous flux impinging on the photodetector at both wavelengths. This requirement follows from the characteristics of the fluorescent labels described hereinabove and the fact that the apparatus of the present invention is intended to be usable in an environment where the wells of microtitration plate 17 may contain serum substances which autofluoresce at wavelengths in the range from 500 to 520 nanometers. In the preferred embodiment, each of the photodetectors of array 16 is a type HEDS-1000 currently manufactured by Hewlett-Packard Incorporated, Optoelectronics Division, of Palo Alto, Calif. A frequency response curve of the voltage output of this particular optodetector is shown in FIG. 5 under conditions of constant luminous flux.

Thus it will be appreciated that the type HEDS-1000 meets the criteria set forth above for photodetectors used in the apparatus of the present invention.

Also shown in FIG. 1 is the remainder of the apparatus for the first preferred embodiment. Another eight by twelve array of elements is shown as 19. Each of the elements of array 19 is a conventional termination for one of a group of ninety-six fiber optic links 20 which carries light from a source of ultraviolet light 21. It is to be understood that ultraviolet light 21 is a conventional fluorescent ultraviolet light and comprises a source of excitation radiation.

Fiberoptics 20 comprise a plurality of light conducting fibers, each being arranged to accept the excitation radiation from ultraviolet source 21 at one end of the fiber and transmitting it to the termination at terminal array 19. It should be understood that each element of terminal array 19 is a polished end of one of the fibers of fiber optic cable 20. It should further be appreciated from inspection of FIG. 1 that each fiber of cable 20 is joined to terminal array 19 in a way which causes each of the fibers to be joined to one of terminals in an array defining a predetermined spaced relationship to the remainder of the fibers.

In use, it will be appreciated that terminal block 19 is set over microtitration plate 17 so that one element of each of arrays 16, 17 and 19 are lined up in a manner which places their approximate geometric centers on the same line.

Thus it will be appreciated that when the arrangement is connected, and each well of microtitration plate 17 contains a sample prepared as described hereinabove, each of the conductors of cable 18 will carry a voltage proportional to the luminous flux of approximately 680 nanometers impinging on the element of photodetector array 16 to which the particular conductor is connected.

A block diagram of the first preferred embodiment is shown in FIG. 2. Ultraviolet source 21 is shown as connected thorugh fiber optic cable 20, only three fibers of which are shown, to a plurality of terminations 22 as previously described. Microtitration well array 17 is set on top of photodetector array 16, the outputs of which are coupled by cable 18 to multiplexer and analog to digital converter block 25. Multiplexer and analog to digital block 25 is connected for bidirectional communication via link 26 to M68MM19 computer board 28 described hereinabove.

Keyboard 15 provides input to one board computer 28 which communicates bidirectionally with the aforementioned disk storage shown as 11' in FIG. 2.

Also shown in FIG. 2 is a printer 29 used for providing hard copies of the results of the assays.

FIG. 3 shows a second preferred embodiment of the present invention which will be understood to be a less expensive, simpler arrangement for performing the tests of the present invention one at a time. It will be apparent that in using the apparatus of the second preferred embodiment, it will be necessary to perform calculations for the dose response curve externally.

As may be seen from FIG. 3, the second preferred embodiment comprises an ultraviolet source 21' which illuminates a microtiter well (or a curvette) 30 under which placed a photodetector 31. It may be seen from FIG. 3 that ultraviolet source 21, microliter well 30, and photodetector 31, all lie substantially on longitudinal axis 37 shown in FIG. 3. The output of photodetector 31 is provided to level adjustment amplifier 32, the output of which is provided to an integrated circuit digital multimeter 35.

In the preferred embodiment, digital multimeter circuit 35 is embodied by an ADD3501 digital multimeter chip currently manufactured by National Semiconductor Corporation of Santa Clara, Calif.

The output of the DMM chip 35 is connected to a three and one-half digit seven segment display 36 so as to provide a numeral indication of the amount of luminous flux at the predetermined wavelength (preferably 680 nanometers) emitted by ths substance contained in microtiter well 30. It is of course apparent that level adjust amplifier 32 should be adjusted to provide an output appropriately scaled to suit three and one-half digit seven segment output 36.

FIG. 4 shows the preferred embodiment of multiplexer and analog to digital converter block 25 together with an exemplary well from microtitration well plate 17. As shown in FIG. 4, ultraviolet lamp 21 is connected by fiber optic cable 20 having ninety-six elements to the terminal block array 19. An exemplary fiber optic element 46 is shown as connected to one of polished terminal connectors 22 which will be understood to be one of such terminations of array 19 shown in FIG. 1.

Enclosed in a box identified as 39 is one of the photodetectors of photodetector array 16. The electrical output of which appears on line 18' which will be understood to be one conductor of cable 18 shown in FIGS. 1 and 2.

The output from line 18' is connected as one input to sixteen channel multiplexer 41c, the other fifteen inputs of which are designated as 40c and will be understood to be connected to conductors of cable 18. Similarly, sixteen additional channels are provided by multiplexers 41a and 41b. The inputs to these multiplexers are 40a and 40b, resepectively, and also are connected to cable 18. Since multiplexer block 25 shown in FIG. 4 has a capacity of thirty-two channels, it will be readily appreciated that the arrangement shown as 25 is a typical one of three identical such boards used in the preferred embodiment to provide the ability to multiplex, one at a time, the outputs of all ninety-six elements of photodetector array 16.

Multiplexer board 25 comprises a programmable gain amplifier 42 which amplifies the outputs from multiplexers 41a–41c. The output of amplifier 42 is provided to sample and hold gate 47, the output of which appears on line 48 as the analog input to twelve bit analog to digital converter 49. The timing and conversion is controlled by conversion control block 50.

The output of A/D converter 49 is provided on line 51 to eight tristate buffers 52 which interface board 25 with the eight bit data bus 55 connected to the aforementioned single board microcomputer. An eight bit bus 56 carries data words, when appropriately addressed, to mode control block 57 and gain and multiplexer control 58. Mode control block 57 controls the particular sequence of signals which must appear on the address and data buses of the system to operate conversion controller 50 to cause the analog to digital conversions to take place.

An address buffer and board select decoder switches are designated as 59 in FIG. 4. While no connections are shown, it should be understood that outputs form this block control the particular elements on board 25 into which data is written or from which it is read during any particular input/output cycle from the single board computer.

It should be appreciated by those skilled in the art that the preferred form of board 25 shown in FIG. 4 is available as a module as model No. M68MM15A currently manufactured by Motorola Semiconductor Products, Inc. of Phoenix, Ariz.

In examining the typical arrangement of polished terminal 22, microtiter well 38, and photodetector 39 it should be noted that at the point of termination 22 of fiberoptic element 46, fiberoptic 46 is characterized by longitudinal axis 45. As shown in the drawing, photodetector 39 lies on longitudinal axis 45 and microtiter well 22 is interposed between termination 22 and photodetector 39 so that longitudinal axis 49 passes substantially through the center of the microtiter well.

I claim:

1. A fluorescent labeled reagent comprising an assay reagent conjugated with an isolated chlorophyll having a Stokes shift of not less than 150 nanometers, said assay reagent being selected from the group consisting of antibodies, antigens, hormones, virus particles, haptens, bacterial components, drugs, monoclonal antibodies, anti-antibodies, immunoglobulins and proteins.

2. The fluorescent labeled reagent of claim 1 wherein the chlorophyll is selected from the group consisting of chlorophyll a, chlorophyll b, chlorophyll $c_1$, chlorophyll $c_2$, chlorophyll d, protochlorophyll and chlorobium chlorophyll.

3. The fluorescent labeled reagent of claim 1 wherein the chlorophyll is selected from the group consisting of Bacteriochlorophyll $a_p$, Bacteriochlorophyll b.

4. The fluorescent labeled reagent of claim 1 wherein the assay reagent is an antigen.

5. The fluorescent labeled reagent of claim 1, wherein the assay reagent is selected from the group consisting of thyroxin, triiodothyronine, thyroid stimulating hormone, thyroxin binding globulins, thyrotropin releasing hormone, digoxin, Gentamicin, Tobramycin, Phenytoin, Theophylline, Tetracycline, Hepatitis B surface antigen, Hepatitus B core antigen, Prostatic acid phosphatase and Human chorionic gonadotropin.

* * * * *